United States Patent
Dehler et al.

(10) Patent No.: US 8,335,296 B2
(45) Date of Patent: Dec. 18, 2012

(54) MULTI-LEAF COLLIMATORS AND OPERATING METHOD

(75) Inventors: Markus Dehler, München (DE); Franz Dirauf, Ebensfeld (DE); Bernhard Gottlieb, München (DE); Andreas Kappel, Brunnthal (DE); Donal Medlar, Weisendorf (DE); Carsten Wallenhauer, Schwarzheide (DE); Björn Werner, Bautzen (DE)

(73) Assignee: Siemens Aktiengesellschaft, Munich (DE)

( * ) Notice: Subject to any disclaimer, the term of this patent is extended or adjusted under 35 U.S.C. 154(b) by 102 days.

(21) Appl. No.: 12/678,411

(22) PCT Filed: Sep. 25, 2007

(86) PCT No.: PCT/EP2007/060142
§ 371 (c)(1),
(2), (4) Date: Jun. 14, 2010

(87) PCT Pub. No.: WO2009/036813
PCT Pub. Date: Mar. 26, 2009

(65) Prior Publication Data
US 2010/0278310 A1  Nov. 4, 2010

(30) Foreign Application Priority Data
Sep. 17, 2007  (EP) .................................. 07018232

(51) Int. Cl.
*G21K 1/04* (2006.01)
(52) U.S. Cl. .................... 378/152; 378/150; 378/151
(58) Field of Classification Search ................ 378/65, 378/147, 150, 151, 152, 153
See application file for complete search history.

(56) References Cited

U.S. PATENT DOCUMENTS

| | | | | |
|---|---|---|---|---|
| 4,794,629 A * | 12/1988 | Pastyr et al. | ................ | 378/152 |
| 5,555,283 A * | 9/1996 | Shiu et al. | ................ | 378/151 |
| 5,557,107 A | 9/1996 | Carcreff et al. | ................ | 250/361 |
| 6,711,237 B1 * | 3/2004 | Schlegel et al. | ................ | 378/152 |
| 6,792,078 B2 * | 9/2004 | Kato et al. | ................ | 378/152 |
| 7,167,542 B2 * | 1/2007 | Juschka et al. | ................ | 378/152 |
| 7,386,099 B1 * | 6/2008 | Kasper et al. | ................ | 378/152 |
| 7,596,209 B2 * | 9/2009 | Perkins | ................ | 378/152 |
| 7,792,252 B2 * | 9/2010 | Bohn | ................ | 378/152 |
| 2003/0063266 A1 | 4/2003 | Leenders et al. | ................ | 355/53 |
| 2006/0067480 A1 | 3/2006 | Juschka et al. | ................ | 378/150 |

FOREIGN PATENT DOCUMENTS

| | | |
|---|---|---|
| JP | 60229680 A | 11/1985 |
| JP | 4308481 A | 10/1992 |
| JP | 2002224230 A | 8/2002 |
| JP | 2002224260 A | 8/2002 |

OTHER PUBLICATIONS

International Search Report and Written Opinion for Application No. PCT/EP2007/060142 (11 pages), Oct. 6, 2008.

* cited by examiner

*Primary Examiner* — Allen C. Ho
(74) *Attorney, Agent, or Firm* — King & Spalding L.L.P.

(57) ABSTRACT

Multi-leaf collimators have a guide frame (1) with a plurality of metal plates (3) arranged in a displaceable fashion, by which each individual metal plate can be displaced by an electric motor (M), with the electric motor (M) being a rotary electromechanical motor (M), which operates according to the form-fit principle, with electromechanical actuators.

9 Claims, 6 Drawing Sheets

MULTI-LEAF COLLIMATORS AND OPERATING METHOD

CROSS-REFERENCE TO RELATED APPLICATIONS

This application is a U.S. National Stage Application of International Application No. PCT/EP2007/060142 filed Sep. 25, 2007, which designates the United States of America, and claims priority to EP Application No. 07018232.4 filed Sep. 17, 2007, the contents of which are hereby incorporated by reference in their entirety.

TECHNICAL FIELD

The invention relates to multi-leaf collimators (MLC)/multi-plate collimators, which are functionally-definitive elements in large devices for radiation therapy.

BACKGROUND

The high-energy radiation generated by an x-ray source, a linear accelerator for instance, such as gamma, x-ray or photon radiation, is shielded by an adjustable diaphragm system, which generally consists of wolfram plates and the beam cross-section is formed, so-called "beam shaping" such that a target area, like a tumor for instance, is exposed to a maximum amount of radiation and surrounding healthy tissue is exposed to a minimum amount of radiation. To achieve the best possible adjustment of the beam cross-section to the target area, the multi-leaf collimator consists of a plurality, for instance several hundred, adjustable thin individual plates. The radiation path in a radiation therapy device consists of a high-energy radiation source, which generates and emits high-energy radiation, a linear accelerator for instance. One first simple electrically adjustable XY diaphragm system limits the radiation path such that the adjacent multi-leaf collimator in the radiation path is fully illuminated. The multi-leaf collimator then structures the beam cross-section such that a precisely predetermined region is radiated.

The optimization problem within radiation therapy consists in minimizing the radiation dose, to which the healthy tissue is exposed, and in at least maintaining it to below a harmful threshold and in simultaneously exposing cancerous tissue to a significantly harmful radiation dose. The methods for radiation treatment are thus very different and are undergoing constant development. Examples worth mentioning here are:
  Conformal Radio Therapy (CRT),
  Intensity-Modulated Radiation Therapy (IMRT),
  Image-Guided Radiation Therapy (IGRT) Gated treatments,
  High-precision radiation therapy and radiation surgery (SRT/SRS),
  Future advanced adaptive therapies, such as Dose-Guided Radiation Therapy (DGRT), as they become available.

The objectives here are to increase selectivity, expand the application bandwidths, such as radiating moving target areas for instance, increasing the operating reliability, such as increasing/extending the service intervals and shortening the treatment duration, such as for instance by "sliding window". In particular, the latter method not only reduces the radiation exposure of the healthy tissue, but also influences the workflow and efficiency of the large devices. The following profile of requirements results herefrom for multi-leaf collimators:
  High positioning accuracy of the wolfram plates (previously type 0.1 mm),
  High movement speed of the wolfram plates (previously type 18 mm/s),
  High acceleration of the wolfram plates (previously type 38 mm/s$^2$),
  High operating reliability/maintenance intervals (life-cycle costs).

DC motors with front-sided planetary gears are currently used as multi-leaf drives with a reduction of 1:275 for instance and a torque of 0.84 Nm at a maximum of 0.44 rps, said DC motors being arranged in groups of type 40 motors and driving the wolfram diaphragms over slanted-toothed helical pinions. Two linear potentiometers are present per diaphragm in order to control and monitor the position. The positioning accuracy amounts to 0.5 mm in the isocenter, which corresponds to a control accuracy of the plates of 0.25 mm.

The prior art consists in radiating cancerous tissue from different spatial directions, with the so-called "step and shoot" strategy being used. The system is thus paused for each new adjustment. In this way, a spatial direction is displaced, the multi-leaf collimator is set up to generate the optimum beam cross-section, and radiates according to a previously determined radiation dose, the next position is displaced and the multi-leaf collimator is set up again etc. A very long treatment duration results due to the added setup times for the individual illuminations.

The aim is to radiate continuously using a rotating gantry/frame and a dynamically variable multi-leaf collimator with a "sliding-window". For devices of the next generation, higher adjustment speeds of more than 20 mm/s are aimed at while simultaneously improving plate positioning accuracy by more than 0.10 mm. These requirements are not restricted or only to a minimum degree using current drive technology and can be costly to display.

The problem involved with using electrical motors for displacing the metal plates consists in the high moment of inertia of the rotor, the high rotor speed and thus a high rotation energy, thereby resulting in poor dynamic characteristics. For this reason, braking or reversing the direction of movement of the metal plates is associated with relatively large delay times. In order to reduce the high rotor speed from type 10,000 rpm to a typical output speed of 60 rpm, electric motors also require a multi-stage gear. As a result of the unavoidable gearbox clearance, the positioning accuracy of the output is restricted, also in fact when an additional sensor is used for position detection purposes.

SUMMARY

According to various embodiments, a multi-leaf collimator can be provided with essentially increased positioning accuracy as known in the prior art.

According to an embodiment, a multi-leaf collimator may comprise a guide frame with a plurality of metal plates arranged in a displaceable fashion, by means of which each individual metal plate can be displaced using an electric motor, wherein the electrical motor is a rotatory electromechanical motor, operating according to the form-fit principle, with electromechanical actuators.

According to a further embodiment, the piezoelectric actuators can be selected from the group of electromechanical actuators consisting of piezoelectric actuators, electrostrictive actuators and magnetostrictive actuators. According to a further embodiment, the piezoelectric motor may comprise at least two electromechanical piezoactuators and an internally toothed driving ring, which can be excited by a stroke of the electromechanical actuators to a circulating displacement movement and an externally toothed shaft which can be attached to the driving ring, so that the shaft can be rotated by means of the displacement movement of the driving ring. According to a further embodiment, a number of piezo-electric actuators, drive rings and shafts can be arranged in a motor housing. According to a further embodiment, the shaft of the piezoelectric motor and the metal plates may comprise intermeshing toothing systems, so that the rotation of the shaft can be converted into a linear movement of the metal plates. According to a further embodiment, the positioning of the metal plates can be controlled electrically. According to a further embodiment, each metal plate can be mechanically coupled to at least one electrical linear transducer for position monitoring purposes. According to a further embodiment, the positioning of the metal plates can be electrically controlled, with a signal of the at least one electrical linear transducer of each metal plate being used as a control signal. According to a further embodiment, a control electronics system may be remote from the piezoelectric engine such that it is arranged in a region with a radiation dose which is lower compared to that of the piezoelectric motor.

According to another embodiment, in a method for operating a multi-leaf collimator as for example described above, charging signals of the piezoelectric actuators of the piezoelectric motors can be used for function monitoring purposes.

According to another embodiment, in a method for operating a multi-leaf collimator as for example described above, metal plates can be moved both individually as well as simultaneously according to individual movement profiles.

According to another embodiment, in a method for operating a multi-leaf collimator as for example described above, piezoactuators can be arranged at right angles to one another and operate according to the longitudinal effect and can be controlled in each instance using a sine/cosine voltage.

BRIEF DESCRIPTION OF THE DRAWINGS

Exemplary embodiments are illustrated below with reference to schematic appending figures, in which.

DETAILED DESCRIPTION

Figure 2:
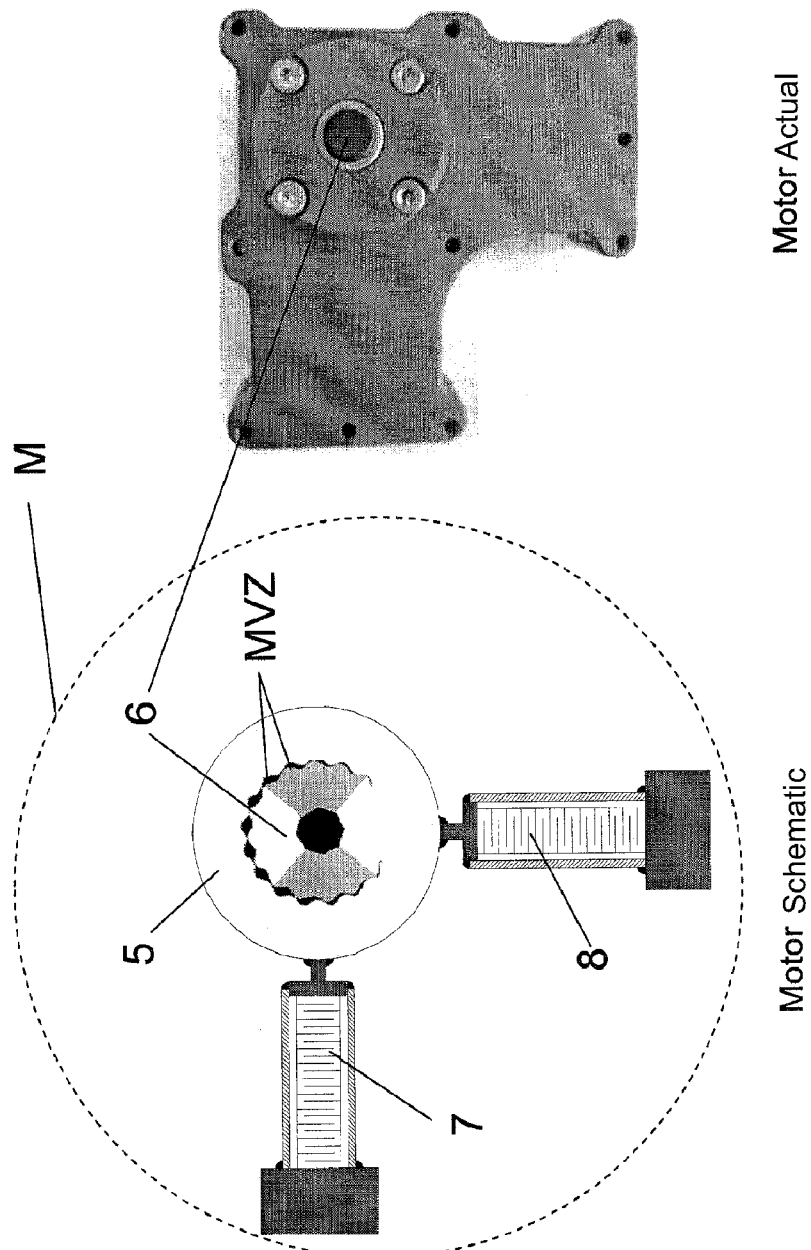
FIG. 2 shows a form-fit operating piezoelectric rotary motor M, schematically and as a real model.

A form-fit operating electromechanical rotary motor M according to FIG. 2 has a lower moment of inertia and less stored rotation energy.

It is advantageous to embody an electromechanical motor shown in FIG. 2 as a piezomotor M, as a result of which it is possible to achieve very rapid changes in movement such as stopping, accelerating, reversing the direction of movement.

As a result of the absent gear and the form-fit power transmission, by means of micro toothing between the driving ring and the motor shaft 6, such a motor achieves very high positioning accuracy, without requiring a linear transducer therefor.

With the motor according to FIG. 2, a sine and cosine voltage are applied in each instance to the at least two piezo actuators 7, 8 arranged at right angles to one another and operating according to the longitudinal effect in order to generate a wave rotation. The precise position of the motor shaft 6 is a function of the absolute phase of the sine and cosine drive voltage. The position can thus be extremely accurately controlled with very little electronic outlay and can be accurately displaced both statistically and also dynamically at any time.

Figure 1:
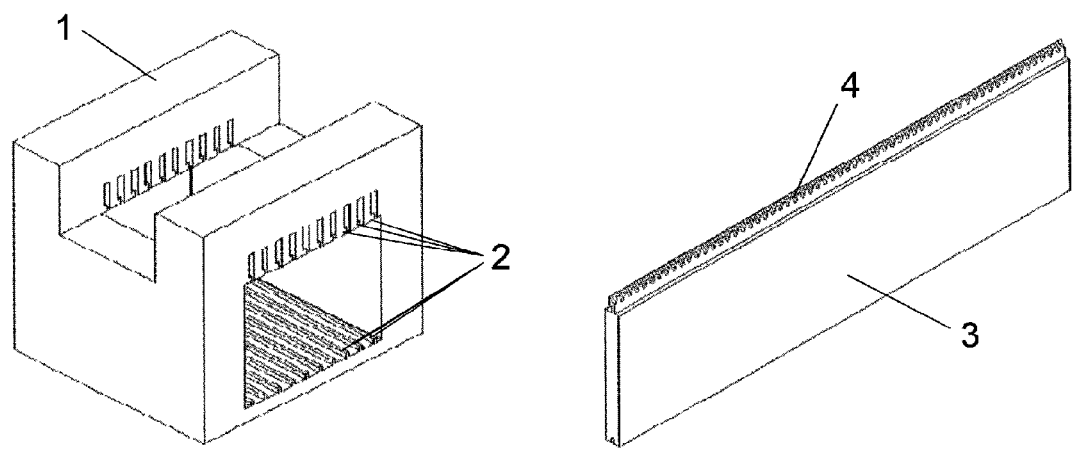
FIG. 1 shows the guide frame 1 of a multi-leaf collimator, with a plurality of guide grooves 2 for receiving metal plates 3.

FIG. 1 shows the guide frame 1 of a multi-leaf collimator, having a plurality of guide grooves 2 for receiving metal plates 3. The metal plates feature toothing 4 on a guide surface located in the direction of movement, into which toothing 4 an electrical drive can engage in order to displace the metal plates in the guide frame.

A form-fit operating piezoelectric rotatory motor M according to FIG. 2 has a low moment of inertia and little stored rotation energy. The piezomotor M shown in FIG. 2 thus enables very rapid changes in movement such as stopping, accelerating, reversing the direction of movement.

As a result of the absent gears and the form-fit power transmission by means of micro toothing between the driving ring 5 and motor shaft 6, such a motor achieves very high positioning accuracy, without requiring a linear transducer herefor.

With the motor according to FIG. 2, a sine and cosine voltage are applied in each instance to the at least two piezo actuators 7, 8 arranged at right angles to one another and operating according to the longitudinal effect in order to generate a shaft rotation. The driving ring 5 is herewith moved in a circular fashion, with the motor shaft 6 rolling along the inner surface of the driving ring 5 in a form-fit fashion.

The precise position of the motor shaft 6 is a function of the absolute phase of the sine and cosine drive voltage. The position can thus be extremely accurately controlled with very little electronic outlay and can be accurately displaced both statistically and also dynamically at any time.

Figure 3:
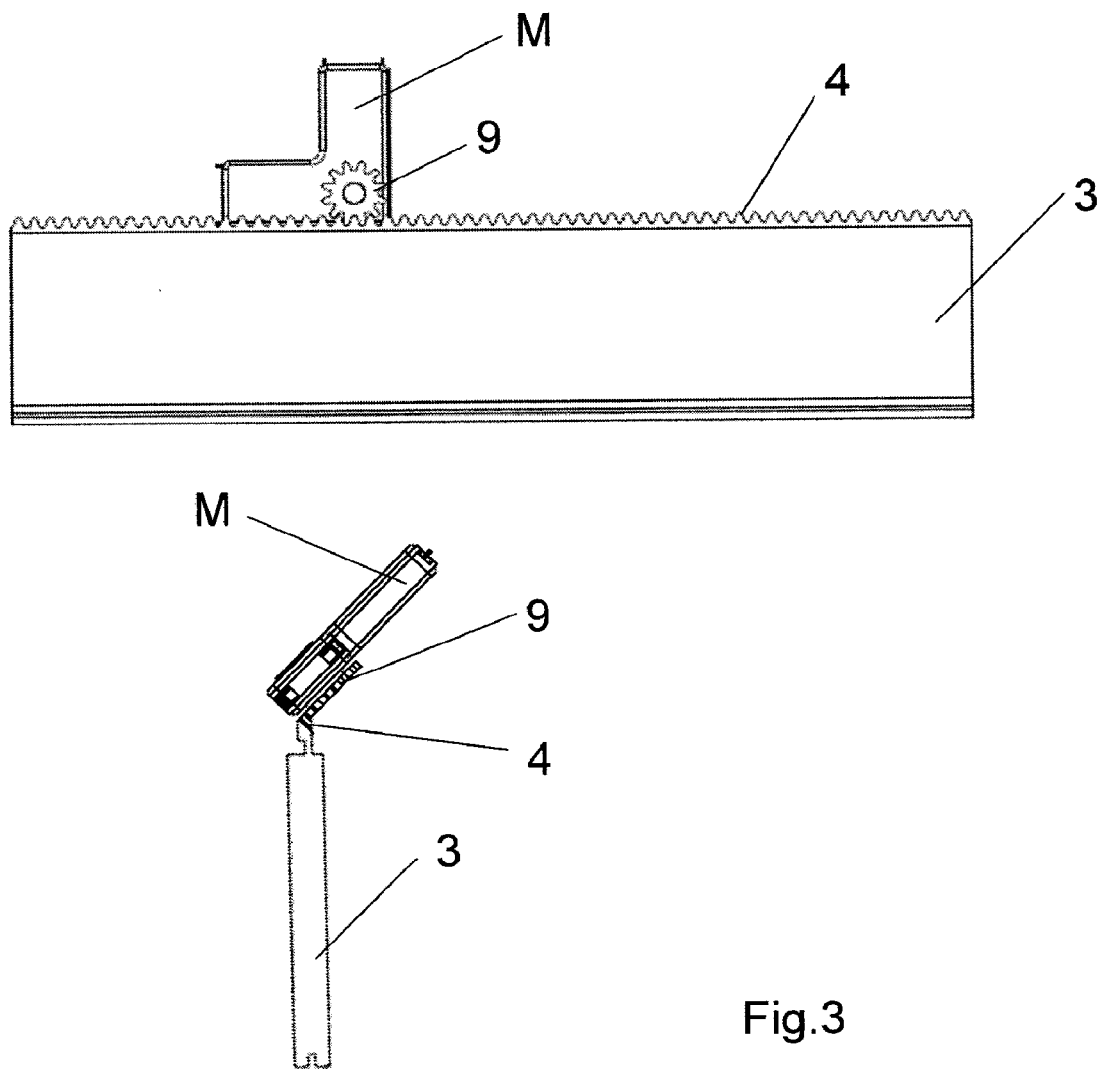
FIG. 3 shows toothing, also helical teeth.

The conversion of the motor shaft rotation 6 into a linear movement of the metal plate 3 is carried out by a toothed wheel 9 which is fastened to the motor shaft, said toothed wheel engaging into the linear toothing of the metal plate, see FIG. 3. In order to optimize the space available, the corresponding toothing can also be helical teeth, as shown for instance in FIG. 3 to FIG. 5.

Figure 4:
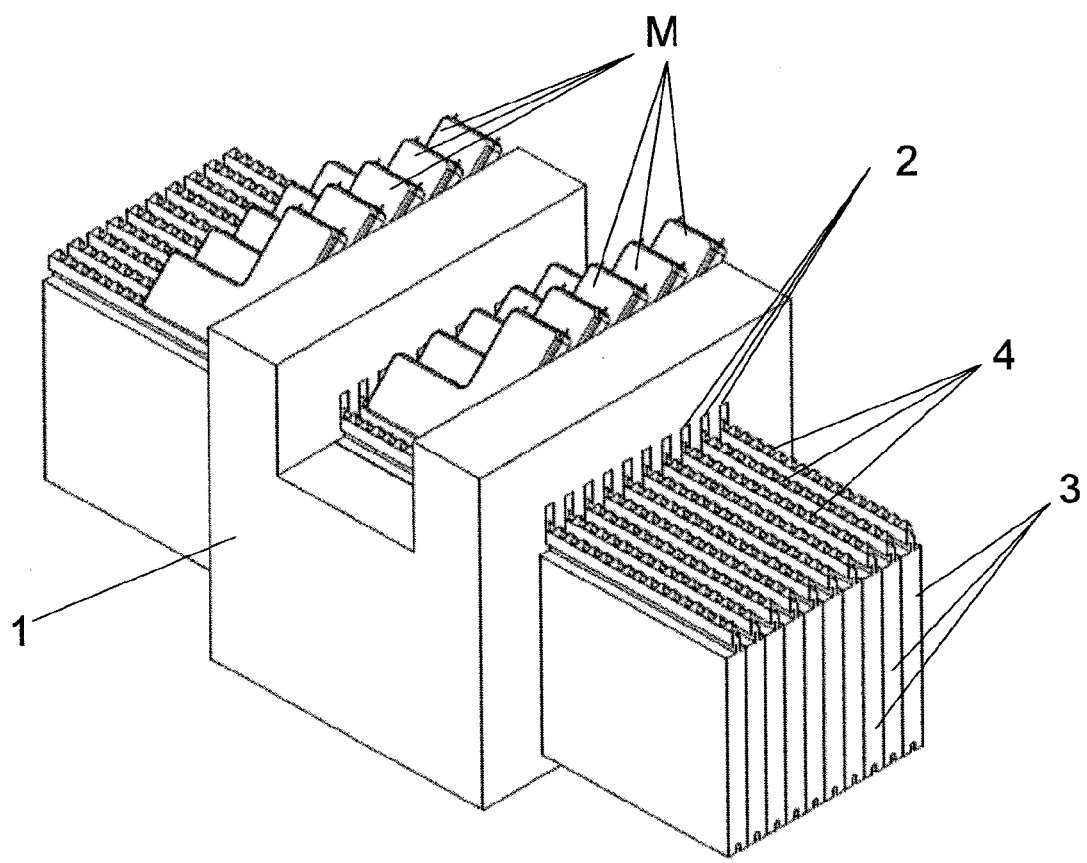
FIG. 4 shows the finished design of a multi-leaf collimator consisting of the guide frame 1, a plurality of guides 2 and metal plates 3 and motors M.

FIG. 4 shows the finished design of a multi-leaf collimator of this type consisting of the guide frame 1, a plurality of guides 2, metal plates 3 and piezo motors M, with a piezomotor driving a metal plate 3 in each instance. The piezo motors M, as shown in FIG. 4, are directly fastened to the guide frame 1 in order to receive the reactive forces. They can however also be fastened to a carrier frame and preassembled as a complete subsystem, which is then, on its part, connected to the guide frame or the housing of the multi-leaf collimator.

Figure 5:
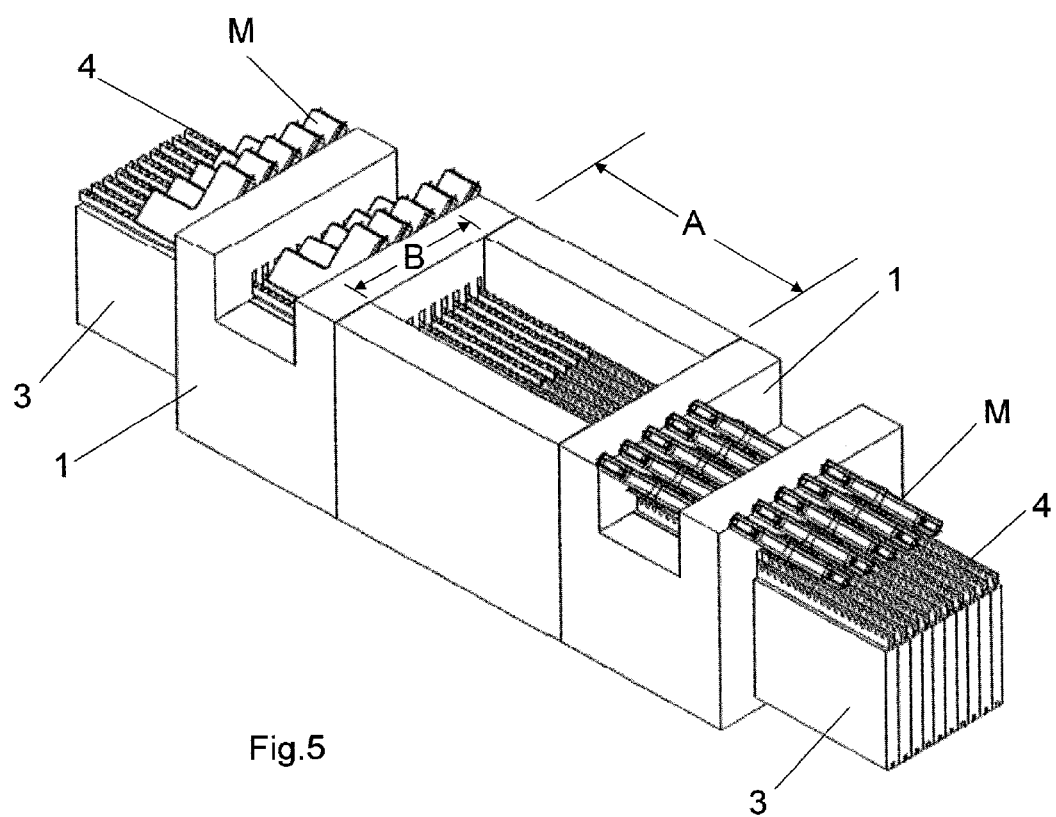
FIG. 5 shows the complete design of a multi-leaf collimator consisting of the mirror-inverted arrangement of two constructions shown in FIG. 4.

FIG. 5 shows the complete design of a multi-leaf collimator—consisting of the mirror-inverted arrangement of two constructions shown in FIG. 4. The multi-leaf collimator shown in FIG. 5 enables, in a window with the diameters A×B, a shaping of the beam cross-section with a transverse resolution according to the width of the metal plates and a longitudinal resolution according to the positional accuracy of the metal plates.

The high absolute accuracy of the form-fit piezomotors renders a complicated control process superfluous, as a result of which the control problem is reduced to purely motor control.

Figure 6:
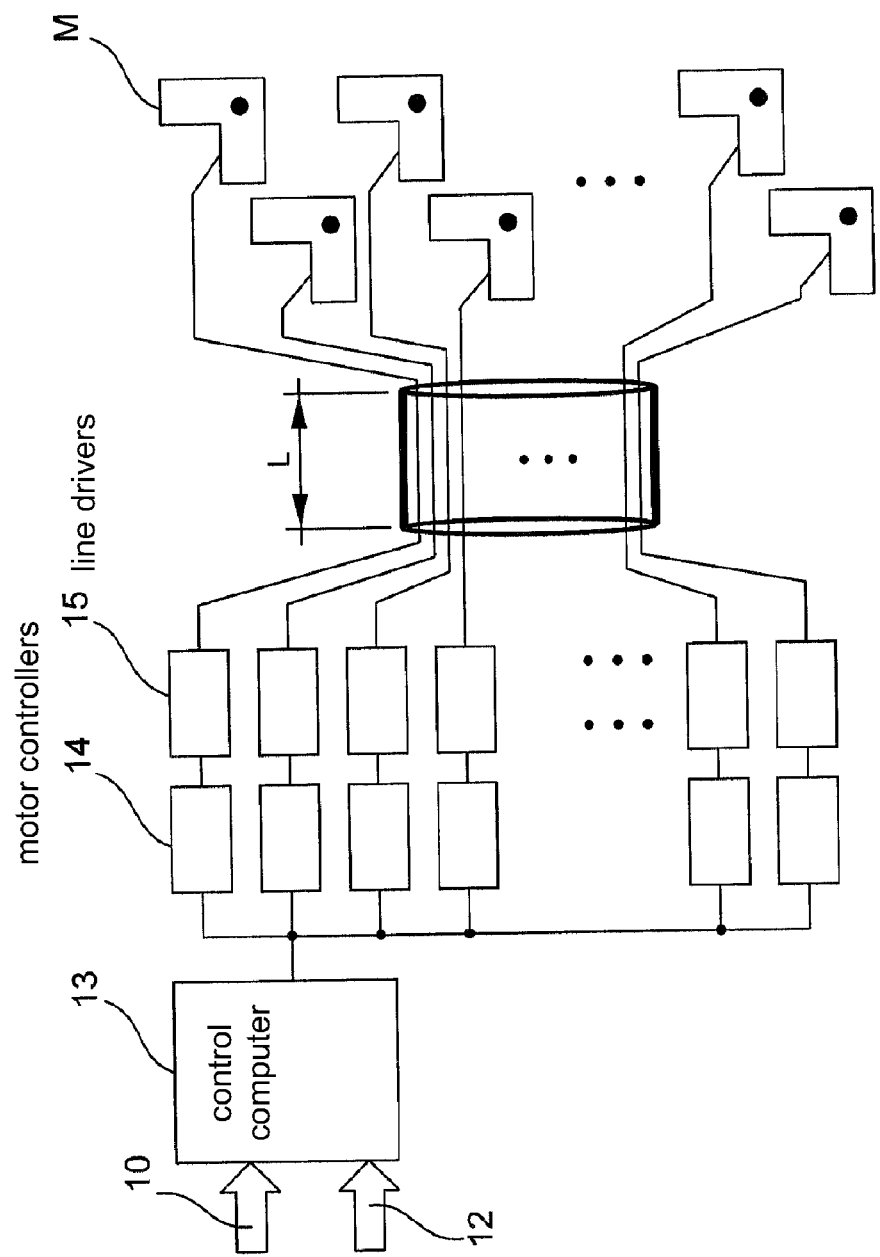
FIG. 6 shows a controlling computer, which controls by way of the information path 10.

The reference character 13 illustrates the controlling computer in FIG. 6, said computer receiving the data of the target area via the information path 10, according to the treatment plan, and receiving the delay angle of the radiation source via the information path 12. The computer 13 uses this data to calculate the optimum position of the individual metal plates in order to adjust the beam contour. The target value for each metal plate and thus for each of the piezomotors M is sent from the computer 13, via a data bus, to the motor controller 14 in digital or analog form. Each motor controller 14 uses the target value to calculate the necessary analogue control signal for the corresponding piezomotor M. The analog motor control signal is transmitted from the motor controller 14 to the line driver 15, which provides the control power needed to drive the piezomotors M. The analog motor control signals are transmitted to the piezomotors M in the multi-leaf collimator by way of lines of length L. As there is no regulation loop and the motor control signals exhibit a high power, in the case of piezoelectric actuators in particular a high voltage amplitude, the connecting line between the piezomotors M and the components of the control electronics 13, 14, 15 can be designed to be comparatively long. The electronics system can herewith be positioned at a great distance from the radiation source, thereby significantly increasing service-life, reliability and service intervals.

A multi-leaf collimator can be provided on each metal plate 3 in order to monitor the position using at least one electrical linear transducer, such as a linear potentiometer for instance, which is mechanically coupled.

What is claimed is:

1. A multi-leaf collimator comprising:
   a guide frame,
   a plurality of metal plates arranged in the guide frame in a displaceable fashion,
   a plurality of piezoelectric motors, each piezoelectric motor including:
      at least two piezoelectric actuators,
      an internally toothed driving ring that is excited by a stroke of the at least two piezoelectric actuators to a circulating displacement movement, and
      an externally toothed shaft attached to the driving ring such that the shaft is rotated by the displacement movement of the driving ring.

2. The multi-leaf collimator according to claim 1, comprising a motor housing that houses a number of the piezo-electric actuators, drive rings and shafts.

3. The multi-leaf collimator according to claim 1, wherein a toothed coupling between each externally toothed shaft and a toothed portion of a corresponding metal plate converts a rotation of the shaft into a linear movement of the metal plate.

4. The multi-leaf collimator according to claim 1, wherein the positioning of the metal plates can be controlled electrically.

5. The multi-leaf collimator according to claim 1, comprising electrical linear transducers for monitoring the position of each metal plate.

6. The multi-leaf collimator according to claim 5, wherein the positioning of the metal plates is electrically controlled, with a signal of the electrical linear transducer of each metal plate being used as a control signal.

7. The multi-leaf collimator according to claim 1, wherein a control electronics system is remote from the electrical motor such that it is arranged in a region with a radiation dose which is lower compared to that of the electrical motor.

8. A method for operating a multi-leaf collimator comprising a guide frame with a plurality of metal plates arranged in a displaceable fashion, and a plurality of piezoelectric motors, each piezoelectric motor including at least two piezoelectric actuators, an internally toothed driving ring that is excited by a stroke of the at least two piezoelectric actuators to a circulator displacement movement, and an externally toothed shaft attached to the driving ring such that the shaft is rotated by the displacement movement of the driving ring, the method comprising:
   controlling the plurality of piezoelectric motors such that at least one of the metal plates is movable both individually and simultaneously according to individual movement profiles.

9. A method for operating a multi-leaf collimator comprising a guide frame with a plurality of metal plates arranged in a displaceable fashion, and a plurality of piezoelectric motors, each piezoelectric motor including at least two piezoelectric actuators, an internally toothed driving ring that is excited by a stroke of the at least two piezoelectric actuators to a circulating displacement movement, and an externally toothed motor shaft attached to the driving ring such that the motor shaft is rotated by the displacement movement of the driving ring, the method comprising:
   for each piezoelectric motor, controlling the at least two piezoelectric actuators using a sine/cosine voltage to control the position of the motor shaft, wherein the at least two piezoelectric actuators are arranged at right angles to one another and operate according to a longitudinal effect.

* * * * *